Figure 7:
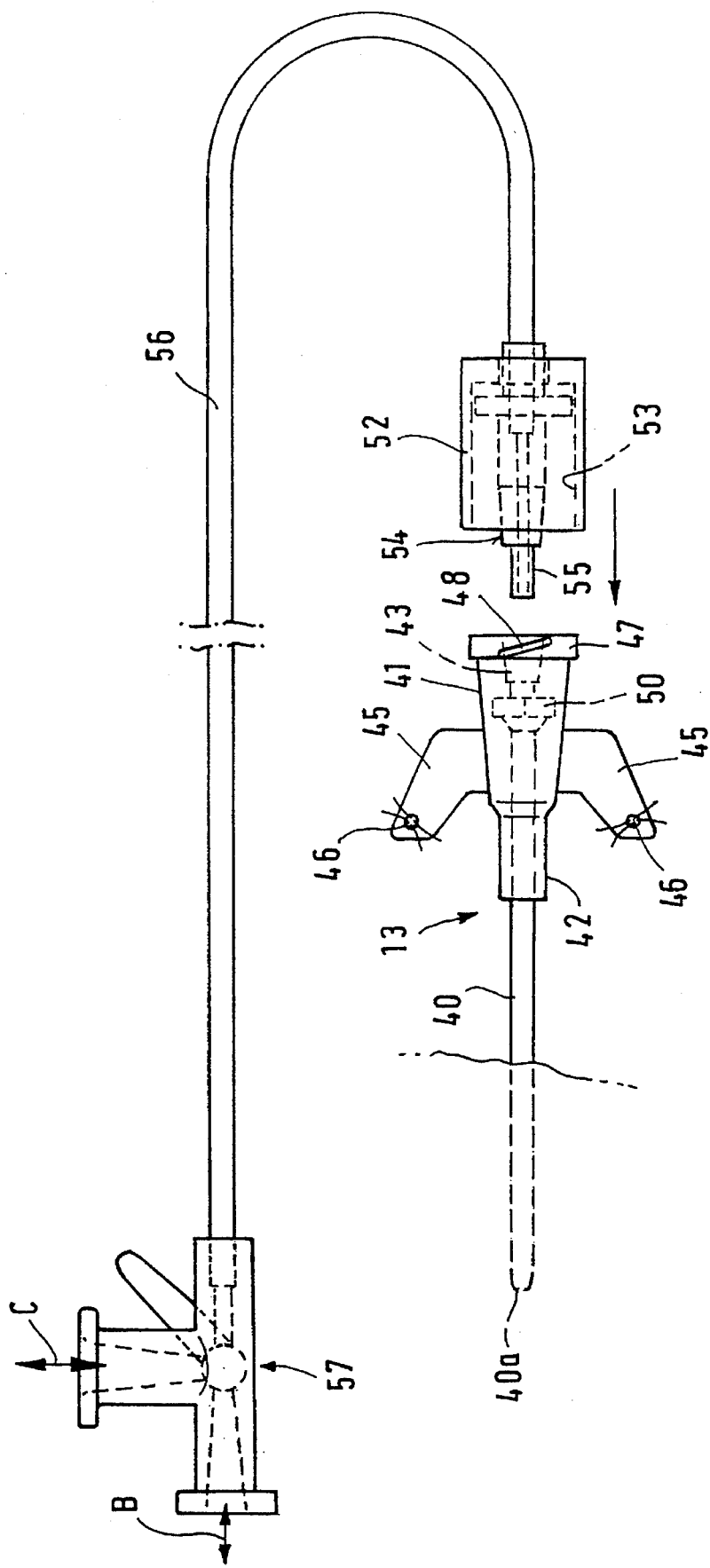

United States Patent [19]

Jesch

[11] Patent Number: 5,512,052
[45] Date of Patent: Apr. 30, 1996

[54] CATHETERIZATION SET

[75] Inventor: Franz Jesch, Krailling, Germany

[73] Assignee: B. Braun Melsungen AG, Melsungen, Germany

[21] Appl. No.: 256,433

[22] PCT Filed: Oct. 13, 1993

[86] PCT No.: PCT/EP93/02813

§ 371 Date: Jul. 1, 1994

§ 102(e) Date: Jul. 1, 1994

[87] PCT Pub. No.: WO94/12233

PCT Pub. Date: Jun. 9, 1994

[30] Foreign Application Priority Data

Nov. 24, 1992 [DE] Germany ............... 9215927 U

[51] Int. Cl.$^6$ ............... A61M 25/06; A61B 17/34
[52] U.S. Cl. ............... 604/158; 604/164
[58] Field of Search ............... 604/165, 158, 604/177, 164

[56] References Cited

U.S. PATENT DOCUMENTS

| 3,680,562 | 8/1972 | Wittes, et al. | |
|---|---|---|---|
| 3,766,916 | 10/1973 | Moorehead et al. | 604/165 |
| 4,191,186 | 3/1980 | Keeler . | |
| 4,230,123 | 10/1980 | Hawkins, Jr. | 604/165 |
| 4,362,156 | 12/1982 | Feller, Jr. et al. | 604/165 |
| 4,735,614 | 4/1988 | Yapp et al. | 604/165 |
| 4,834,708 | 5/1989 | Pillari | 604/165 |
| 4,969,875 | 11/1990 | Ichikawa | 604/158 |
| 4,973,313 | 11/1990 | Katsaros et al. | 604/165 |
| 5,047,018 | 9/1991 | Gay et al. | 604/165 |
| 5,098,392 | 3/1992 | Fleischhacker et al. | 604/165 |
| 5,141,497 | 8/1992 | Erskine | 604/165 |
| 5,163,913 | 11/1992 | Rantanen-Lee et al. | 604/177 |

FOREIGN PATENT DOCUMENTS

| 89152999 | 3/1990 | Denmark . |
| 0161636 | 11/1984 | European Pat. Off. . |
| 0129745 | 1/1985 | European Pat. Off. . |
| 0352928 | 1/1990 | European Pat. Off. . |
| 0411605 | 2/1991 | European Pat. Off. . |
| 2368968 | 5/1978 | France . |
| 2052364 | 10/1970 | Germany . |
| 89149416 | 11/1990 | Germany . |
| 4208228 | 9/1993 | Germany . |
| 8807388 | 10/1988 | WIPO . |
| 880738 | 10/1988 | WIPO . |
| 9218193 | 10/1992 | WIPO . |
| 93111812 | 6/1993 | WIPO . |

Primary Examiner—Paul J. Hirsch
Attorney, Agent, or Firm—Loeb & Loeb

[57] ABSTRACT

In a catheterization set for placing a catheter in a blood vessel, comprising a puncture needle (10) with a needle hub (16) carrying a grip device (25), a catheter (13) surrounding the puncture needle (10) and having a catheter hub (41) arranged thereon, and a guide wire (12) axially displaceable in the lumen of the puncture needle (10), it is provided, according to the invention, that a grip means (32) of the grip device (25) is arranged in spaced relationship beside the puncture needle (10). In this manner, the puncturing properties of the catheterization set are improved because the user can rest his hand performing the puncture in the immediate vicinity of the puncture site.

3 Claims, 3 Drawing Sheets

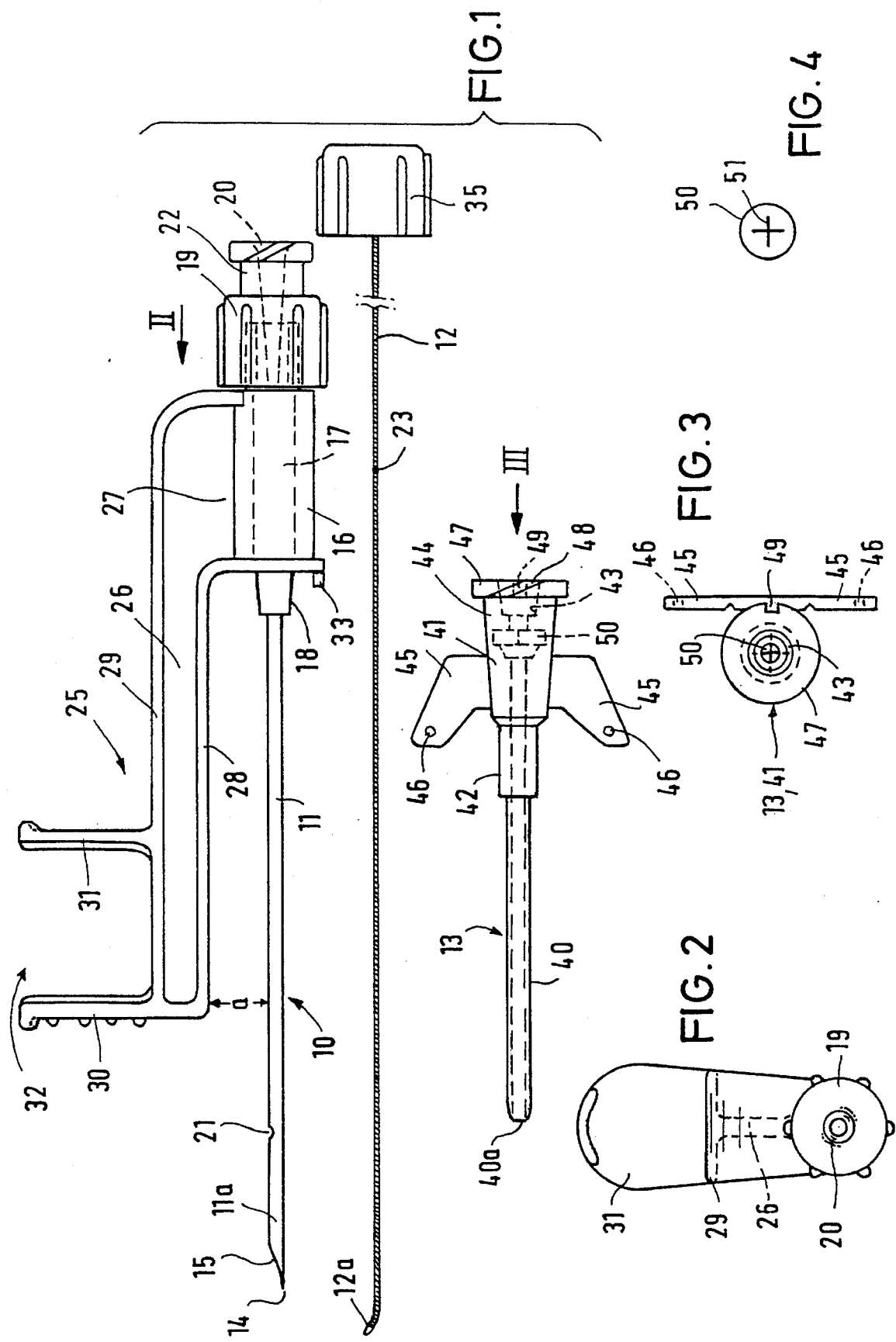

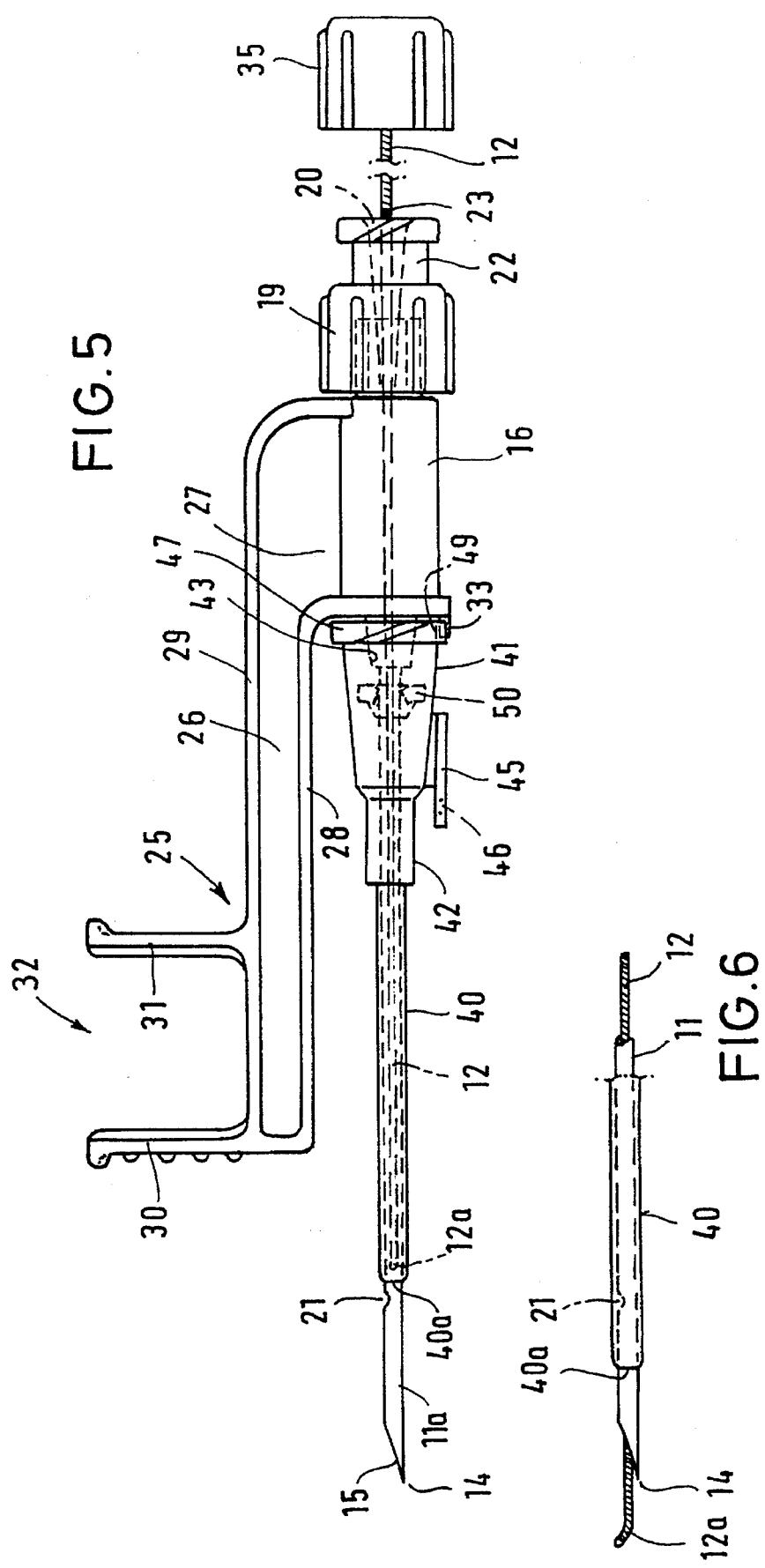

CATHETERIZATION SET

The present invention is directed to a catheterization set for placing a catheter in a blood vessel, comprising a puncture needle provided with a needle hub carrying a grip device, a catheter surrounding the puncture needle and having a catheter hub arranged thereon, and a guide wire to be axially displaced in the lumen of the puncture needle.

For measurement of pressures in vessels (arterial blood pressure), administration of infusions and blood sampling, it is required that arteries and central veins be punctured and so-called in-dwelling catheters be set, which are provided as short catheters having a catheter hub for connection to a liquid transfer device. The catheter accommodates a puncture needle with its ground tip slightly protruding beyond the front end of the catheter. A set of this type is known from U.S. Pat. No. 3,312,220. For obtaining a smooth transition from the puncture needle to the thicker catheter during puncture, the tip of the catheter is on the outside beveled towards the front. However, the continuous transition from the catheter to the outer periphery of the puncture needle is not capable of avoiding a disadvantageous widening of the puncture hole and the difficulties in penetrating the skin and the vessel wall, resulting in reduced precision of the puncture. This setback is all the more aggravating since this known set lacks a grip device so that the set has to be gripped directly on the cylindrical needle hub, which does not allow for a firm hold of the set.

Frequently, it is suitable to use a guide wire for placement of the catheter. This guide wire is has a greater length than the catheter. For avoiding injuries to the patient, guide wires have a soft tip. Advantageously, the guide wire, being stiffer than the catheter, can be advanced into the vessel with higher aiming accuracy than the catheter and at the same time stiffens the catheter being advanced on it and moves the catheter to its desired location in a controlled manner. This method of placing a catheter is called "Seldinger technique" and is used both in short and long catheters.

Generally, when applying this technique, the blood vessel is first punctured by the set comprising the puncture needle and the short catheter mounted thereon, or by use of a puncture needle alone. Subsequently, the guide wire is shifted into the vessel through the placed puncture needle, and the catheter is then advanced into the vessel while moving over the guide wire. Thereafter, the guide wire is withdrawn and discarded. The separately used components are inconvenient to the user because the threading or plug-on maneuver of the components is time-consuming and requires heightened attention.

To avoid the operational disadvantages of separate components, these were combined into one catheterization set which can be handled as a unit. A catheterization set of this type is described in EP-A-00 93 164. At the rear (proximal) end of this known catheterization set, the needle hub of the puncture needle assembled to the short catheter is provided with a long tube member containing the guide wire. By means of a slider projecting into the interior of the tube member through a slot, the guide wire can be axially displaced to have its front end projecting out of the puncture needle. Because of its considerable length and the lack of a grip device, this catheterization set is difficult in handling, which adversely affects the accuracy of puncture.

The puncture is performed in the retracted condition of the guide wire so that, after successful puncture, blood will flow back within the puncture needle and enter the transparent needle hub. However, since the set is gripped on this needle hub, the fingers of the user block the view onto the needle hub so that the withdrawal of blood into the needle hub will be detected late or not at all. Also this set suffers from the disadvantage that, during puncture, not only the puncture needle but also the catheter surrounding it has to penetrate the puncture hole. Due to the resistance offered by the skin, the penetration of the skin occurs in a sudden jolt-like movement so that an exact placement of the tip of the puncture needle in the vessel is rendered difficult or often impossible.

A certain improvement in checking the success of a puncture is achieved by the set according to U.S. Pat. No. 4,894,052, designed particularly for arterial puncture. In this set, the catheter of consists of a transparent plastic material, and the puncture needle, shifted through the catheter and having only the ground portion of the tip protruding beyond the catheter, accommodates a guide wire displaceably arranged therein. The puncture needle is provided with a lateral hole which, when the catheterization set is ready for use, is located behind the end of the catheter, i.e. is surrounded by it. Upon successful puncture, blood will pass through said hole into an annular space between the puncture needle and the transparent catheter and, when rising in the direction of the hubs, will be visible through the catheter. The necessity of providing an annular space for blood passage results in an enlarged outer diameter of the catheter and thus impairs the puncture of the skin and the vessel wall because the thick catheter causes a jolt-like advance movement, presenting a risk to accurate placement of the tip of the puncture needle in the vessel. Further, the issuing of blood from said hole is not always immediately noticed because the perforated portion sticks in the tissue. The user has to wait for the blood to rise towards the hubs.

A catheterization set is described in EP-A-0 446 804. The handling properties of this catheterization set are improved by a grip device comprising grip plates. The catheter hub and the needle hub each have a respective grip plate arranged thereon, with the planes of the grip plates extending transversely to the longitudinal axis of the set and crossing the front end of the respective hub. Relative to the tip of the puncture needle, the grip plates are displaced far to the rear. Thus, during puncture, a long lever arm will become effective which, although advantageously making it easier to grip the set, impairs a precise puncture of the skin and the vessel wall.

It is an object of the invention to improve catheterization sets in such a manner that their puncturing properties are improved.

Accordingly, the above object is solved in that a grip means of the grip device is arranged in spaced relationship beside the puncture needle.

The grip means of the grip device, displaced in forward direction towards the puncture tip of the puncture needle, provides for a direct application of the advance force to the tip of the puncture needle while penetrating the skin and the vessel wall, resulting in a precise guidance of the puncture needle so as to perform an exact puncture. Gripping and handing of the puncture set are easy because the lever arm between the grip means and the tip of the puncture needle is short and the user can rest his hand performing the puncture in the immediate vicinity of the puncture site, which allows for a considerably increased aiming accuracy. The distance between the grip means and the tip of the puncture needle can be selected to be optimum for the respective application of the catheterization set. Advantageously, at least the front end of the grip means is arranged substantially in the longitudinal center of the puncture needle. The length of the catheter plugged onto the puncture needle is independent from the arrangement of the grip means. In each phase of the application, the catheterization set composed of the puncture needle, the catheter and the guide wire is advanced by the forwardly displaced grip means in a precise manner so that the puncturing and the introducing of the guide wire and the follow-up movement of the catheter over the guide wire are performed without deviation. Thus, the puncturing and the placing of the catheter become safer for the patient and more convenient for the user.

Preferably, the grip means is mounted on an arm which, starting from the needle hub, extends in parallel along the puncture needle. Said arm, the grip means and the needle hub can be integrally formed from a plastic material. Preferably, the arm has flat shape and reinforced edges, the plane of the arm surface crossing the longitudinal axis of the set. Thereby, resilient movements of the arm are prevented, and there is obtained a good transfer of force from the grip means via the needle hub to the tip of the needle.

According to an advantageous embodiment of the invention, the grip means comprises two grip plates arranged in mutual alignment and in parallel to each other and having their planes extending transversely to the longitudinal axis of the set. Both grip plates are seized between the thumb and the index finger of one hand and facilitate the gripping and the transfer of force to the tip of the puncture needle.

A further increase of the puncturing accuracy of a catheterization set with guide wire is obtained in another embodiment.

In this embodiment, it is provided that the tip portion of the steel needle projects beyond the tip of the capillary tube by a length of 15 mm to 25 mm, preferably 20 mm. The puncturing of the artery or vein is performed exclusively by the free, exposed steel portion of the steel needle, thus allowing for precise puncture of the vessel. The capillary tube on the steel needle does not immediately penetrate the skin. Because of the absence of a "step" on the periphery of the steel needle, the penetration of the skin occurs practically jolt-free and in a linear direction so that the tip of the steel needle will be placed as desired by the user. The guided movement of the guide wire to the desired position and the placing of the catheter will be performed with a corresponding degree of exactness.

Using the catheterization set of the invention, the catheter can be introduced according to two methods:

a) introduction through the puncture needle while still inserted in the artery, to obtain better guidance through the skin and the puncture channel, with the guide wire serving for guidance within the lumen of the artery, b) introduction over the guide wire after the puncture needle has been retracted.

Each of the above two methods is enhanced by the good hold on the set offered by the inventive arrangement of the grip means and by the improved puncture accuracy due to the exposed projecting portion of the puncture needle.

According to a further preferred embodiment of the invention, it is provided, that the wall of the steel needle has a hole formed therein before the tip of the catheter. When the guide wire has been pulled back behind said hole while acting to close the lumen, or when the guide wire has been merely retracted into the ground portion while leaving an annular space towards the wall of the needle, a completed puncture of the vessel is immediately indicated by a small quantity of blood issuing from the exposed hole in the steel needle. The user will not lose time by waiting for blood to rise up to the needle hub. If no blood issues from the hole in the steel needle, the user can immediately repeat the puncture. The safety of the puncture is increased. Also the hygienic conditions are improved because undesired leakage of blood at the user-side end is largely prevented. The reduced danger of contamination has a favorable effect on the working conditions. The hole in the steel needle can be formed by drilling, grinding or punching. Preferably, the hole is located in the immediate vicinity of the tip of the catheter so that the exposed portion of the steel needle can be used as a puncture element substantially over its whole length. The size of the hole is to be selected in such a manner that, while issuing blood can be noticed, outflow of larger quantities of blood is prevented.

With the present the invention, the catheterization set may be further improved to the effect that, after the catheter has been placed—particularly in an artery—backflow of blood is precluded whereas a transfer device can be easily connected to the catheter.

For this purpose, a valve body with a self-closing passage is arranged in the catheter hub. The passage formed in the valve body allows the puncture needle with the guide wire therein to pass through it without generation of shavings. When, after completion of the puncture, the puncture needle and the guide wire have been pulled out of the catheter, the passage of the valve body will close, and a backflow of blood from the needle hub will not occur. The catheter can be fixed on the skin of the patient unhurriedly, e.g., by means of fixation wings, without the need to clamp the artery.

Advantageously, the valve body comprises an elastomeric disk with at least one slit formed therein. A connector piece of a tube conduit, provided for connection to the needle hub, includes a coaxial, tubular hold-open device penetrating the slit. In combination with said tubular hold-open device, the connector piece, which can be connected directly to the needle hub, causes the valve body in the needle hub to open. The tube conduit serves for establishing a flexible connection to a transfer device. Thus, the danger of dislocation of the artery is avoided because the tube conduit can be set and handled in a manner avoiding undesired pulling on the catheter lodged in the vessel. Handling is further improved in that the end of the tube conduit facing away from the connector piece is provided with a stopcock, preferably a three-way stopcock, to allow liquid and pressure transfer after opening the passage in the valve body.

A puncture instrument comprising a steel needle having its end provided with a hub and an associated grip means, is characterized in that a grip means of the grip device is arranged in spaced relationship beside the steel needle. The steel needle can be a hollow puncture cannula or a massive trocar cannula, both of which have their distal end provided with a ground puncture tip—in both cases, it is imperative that the cannula can be fixed and guided in a manner allowing precise placement. This is accomplished by arranging the grip means at a distance from the hub and at a displacement towards the puncture tip.

An embodiment of the invention is schematically illustrated in the drawing.

FIG. 1 is a view of three components of a catheterization set to be coaxially mounted to each other for use, FIG. 2 is a view in the direction of arrow II in FIG. 1, FIG. 3 is a view in the direction of arrow III in FIG. 1, FIG. 4 is a plan view of a valve disk for the needle hub, FIG. 5 is a plan view of the catheterization set when ready for use, FIG. 6 is a view of the front end of the catheterization set in the advanced stages of application, and FIG. 7 is a view of the catheter when set in the vessel and sutured to the skin, shortly before the valve in the needle hub is opened by a hold-open device mounted on a connector means.

A catheterization set particularly suited for the catheterization of arteries substantially consists of three components, i.e. a puncture needle 10, a guide wire 12 and a catheter 13. These components can be coaxially assembled as shown in FIG. 5. Puncture needle 10 comprises a hollow steel needle 11 having its front (distal) end 15 pointed and sharpened by grinding. The rear (proximal) end of needle 11 is provided with a needle hub 16 having a channel 17 extending therethrough. An outer cone 18 at the transition between steel needle 11 and needle hub 16 serves as a plug element for connection with an inner cone of a catheter hub of catheter 13. A blood retaining cap 19 with a narrow coaxial passage 20 for guiding the guide wire 12 terminates needle hub 16 at the rear end. The blood retaining cap 19 has its rear end carrying a coaxial coupling piece 22 comprising a locking element for a connection. At a distance of about 18 mm behind the tip 14 of steel needle 11, a small hole 21 is formed—by drilling, grinding or punching—in the wall of needle 11. Hole 21 is a throughhole extending from outside into the lumen of steel needle 11.

A grip device 25 is connected to needle hub 16 of puncture needle 10. Preferably, needle hub 16 and grip device 25 are made from plastic and formed as one piece. Grip device 25 comprises an arm 26 extending parallel to steel needle 11 at a lateral distance therefrom. The rear (proximal) end of arm 26 is joined, via a leg 27 projecting at a right angle, to a tubular main body of needle hub 16. Preferably, the width of leg 27 is substantially equal to the length of said main body. The transverse dimension of the main body determines the distance a between steel needle 11 and the edge 28 of arm 26 closest to steel needle 11. The major portion of arm 26 is of a plate-like, flat shape while its two longitudinal edges 28 and 29 are reinforced in bead-like manner for stabilization. The front (distal) end of arm 26 is formed with two grip plates 30,31 laterally projecting from longitudinal edge 29 at right angles and being in mutual alignment. The two grip plates 30, 31 form a grip means 32 to be gripped between the thumb and the index finger. The length of arm 26 and the attachment of grip means 32 on arm 26 are selected in such a manner that grip means 32 is arranged in the central region of steel needle 11. A preferred distance between tip 14 and grip plates 30 is about 45 mm.

Needle hub 16 and steel needle 11 are adapted to have the guide wire 12 inserted therethrough. The diameter of guide wire 12 is matched with the diameter of the lumen. The proximal end of guide wire 12 carries a headpiece 35 which is formed as a closure cap having an inner thread to be screwed to a threaded portion of coupling piece 22. Guide wire 12 can be provided as a tightly wound steel wire having a flexible tip 12a. Alternatively, the catheterization set is operable also with a guide wire wherein the rear end comprises a rigid length of wire, with only the front end of the guide wire formed as a spirally wound flexible strand. When guide wire 12 has been inserted into puncture needle 10 until abutment of headpiece 35 onto blood retaining cap 19 and, through a twisting movement, has been locked to coupling piece 22 of blood retaining cap 19, the front end of guide wire 12 projects beyond tip 14 of steel needle 11 by a length required for fulfilling the guiding function in the respective application, which length can be about 20 mm to 50 mm.

Catheter 13 is a short catheter made from a flexible plastic, having a length of 45 mm to 50 mm and consisting of a capillary tube 40 with a catheter hub 41 fastened to the rear end thereof. Catheter hub 41 is a tubular body having its front (distal) end provided with a flexible antikink protection means 42 for capillary tube 40 and having its rear (proximal) end formed with an inner cone 43 for receiving the outer cone 18 of puncture needle 10, and with a chamber 44 for accommodating a valve means. Two fixation wings 45, directed to opposite sides and provided with holes 46 for suturing the fixation wings 45 to the skin of the patient, are arranged on the outer side of catheter hub 41.

The rear opening of catheter hub 41 is surrounded by an annular flange 47 comprising coupling elements 48, e.g., threaded portions, to be connected to a connector for connection of external conduits to catheter 13. Annular flange 47 is provided with a radial notch 49 to be engaged by an axial pin 33 of needle hub 16 to preclude rotation. Said chamber 44 has an elastomeric disk 50 seated therein, which is transversed by a slit or cross-slit 51 having its lips arranged close to each other and blocking the channel of catheter 13 in rearward direction.

For shipment of the catheterization set within a sterile packing, catheter 13 is plugged onto puncture needle 10 and is fixed thereon by mutual engagement of outer cone 18 and inner cone 43. In this assembled condition, steel needle 11 has a portion 11a protruding beyond the tip 40a of capillary tube 40 by preferably 20 mm, and hole 21 is free of capillary tip 40a (FIG. 5). Guide wire 12 has been inserted through puncture needle 10 and protrudes from the ground tip 15 of steel needle 11 by a certain length. A protective cap (not illustrated) is provided for shielding the puncture elements to be inserted into the patient.

For puncturing, guide wire 12 is retracted until a marking 23 on guide wire 12 has reached the same longitudinal position as the rear edge of blood retaining cap 19 and the tip 12a of guide wire 12 is located behind hole 21 of steel needle 11 (FIG. 5). The catheterization set is seized by the angled grip means 32, and the steel needle 11 is inserted into a blood vessel exclusively by its free exposed portion 11a which is free of capillary tube 40. Hole 21 remains visible outside the puncture point. Successful puncture will be immediately detected by blood issuing from hole 21. Then, guide wire 12 is advanced into the vessel and its headpiece 35 is engaged with blood retaining cap 19 attached to needle hub 16. The advance movement of guide wire 12 will close hole 21 and terminate the issuing of blood. Further, guide wire 12 largely prevents a backflow of blood because, having its diameter adapted to the lumen of steel needle 11, guide wire 12 acts also to close the lumen. Capillary tube 40 can be advanced into the vessel over guide wire 12 and steel needle 11 which has been slightly retracted from the puncture hole. Subsequently, steel needle 11 and guide wire 12 arranged therein are pulled out of catheter 13 in their entirety. After withdrawal of steel needle 11 and guide wire 12, the cross-slit 51 of the elastomeric disk 50 in catheter hub 41—which, to allow passage of steel needle 11, has easily opened and with its four flaps has engaged the periphery of steel needle 11 in a sealing manner—will return to a closed position to provide a sealing against blood backflow from catheter 13. Using the fixation wings 45, catheter 13 is sutured to the skin of the patient so that the tip 40a of capillary tube 40 is fixed in the correct position within the vessel.

For connection of a transfer device to catheter 13, a flexible tube conduit 56 is used, one end of which is connected to the casing of a three-way stopcock 57 having inlet/outlet ports B and C (FIG. 7). The other end of tube conduit 56 is provided with a connector piece 52 having an inner thread 53 to be screwed onto the coupling elements 48 of the annular flange 47 of catheter hub 41. A coaxial outer cone 54, fitting into the inner cone 43 of catheter hub 41, is extended in outward direction by a tubular hold-open device 55. In the connected state of components 41 and 52, this very small-dimensioned hold-open device 55 penetrates the cross-slit 51 of elastomeric disk 50 and keeps the valve body 50 open to allow liquid flow therethrough. By switching the three-way stopcock 57, the inlet/outlet ports B and C are opened or closed, respectively.

I claim:

1. A catheterization set for placing a catheter in a blood vessel, comprising:

a puncture needle comprising a lumen and a needle hub carrying a grip device, a catheter comprising a capillary tube and a catheter hub and being configured to surround the puncture needle, an arm extending in a direction substantially parallel to the puncture needle from the needle hub to a location beyond the catheter hub, grip means arranged on the arm at a location beyond the catheter hub and in spaced relationship with the puncture needle, whereby the grip means overlays the capillary tube.

2. The catheterization set of claim 1, wherein the catheterization set defines a longitudinal axis and wherein the grip means comprises two mutually parallel grip plates extending substantially transversely to the longitudinal axis of the catheterization set.

3. A puncture instrument, comprising:

a needle having a longitudinal axis and an end provided with a hub, an arm extending from the hub in a direction substantially parallel to the needle, grip means arranged on the arm in spaced relationship with the needle, the grip means comprising two mutually parallel grip plates extending substantially transversely to the longitudinal axis of the needle.

* * * * *